(12) United States Patent
Whitman

(10) Patent No.: US 6,716,230 B2
(45) Date of Patent: *Apr. 6, 2004

(54) VESSEL AND LUMEN EXPANDER ATTACHMENT FOR USE WITH AN ELECTROMECHANICAL DRIVER DEVICE

(75) Inventor: Michael P. Whitman, New Hope, PA (US)

(73) Assignee: Power Medical Interventions, Inc., New Hope, PA (US)

( * ) Notice: Subject to any disclaimer, the term of this patent is extended or adjusted under 35 U.S.C. 154(b) by 104 days.

This patent is subject to a terminal disclaimer.

(21) Appl. No.: 09/990,067

(22) Filed: Nov. 21, 2001

(65) Prior Publication Data

US 2002/0052623 A1 May 2, 2002

Related U.S. Application Data

(63) Continuation of application No. 09/510,926, filed on Feb. 22, 2000, now Pat. No. 6,348,061.

(51) Int. Cl.[7] .............................................. A61M 29/00
(52) U.S. Cl. ...................................... 606/198; 604/109
(58) Field of Search ................................ 606/198, 191, 606/159, 108; 604/105, 106, 107, 108, 109

(56) References Cited

U.S. PATENT DOCUMENTS

| | | |
|---|---|---|
| 3,193,165 A | 7/1965 | Akhalaya et al. |
| 3,256,875 A | 6/1966 | Tsepelev et al. |
| 3,388,847 A | 6/1968 | Kasulin et al. |
| 3,494,533 A | 2/1970 | Green et al. |
| 3,552,626 A | 1/1971 | Astafiev et al. |
| 3,568,659 A | 3/1971 | Karnegis |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 4,071,029 A | 1/1978 | Richmond et al. |
| 4,085,756 A | 4/1978 | Weaver |
| 4,198,960 A | 4/1980 | Utsugi |
| 4,198,982 A | 4/1980 | Fortner et al. |
| 4,202,479 A | 5/1980 | Razgulov et al. |

(List continued on next page.)

FOREIGN PATENT DOCUMENTS

| | | |
|---|---|---|
| DE | 33 00 768 | 7/1984 |
| EP | 0 116 220 | 8/1984 |
| EP | 0 156 774 | 10/1985 |

(List continued on next page.)

Primary Examiner—Kevin T. Truong
(74) Attorney, Agent, or Firm—Kenyon & Kenyon (57) ABSTRACT

A selectively coupleable and remotely actuateable surgical attachment for use with an electromechanical driver device for use in expanding occluded vessels and lumens. The attachment includes an axial rod which is coupleable to the electromechanical driver device, and which is selectively rotateable in accordance with the action of the electromechanical driver device. The rod is also threaded in opposing orientations at either end thereof. A pair of nuts are mounted to the rod, and specifically on the opposing threads. The rod and nuts are disposed within an axial track which permits the rod to turn, but constrains the rotational motion of the nuts, thereby permitting the nuts to move axially along the threadings of the rod when the rod turns. Attached to the nuts are a series of jointed spokes which are coupled to a flexible tubular shroud which surrounds the entire assembly. The jointed spokes are radially extended and retracted in accordance with the motion of the nuts in an umbrella-like fashion in accordance with the actuation of the electromechanical driver device. The radial expansion of the flexible tubular shroud provides the necessary force to expand an occluded vessel or lumen.

29 Claims, 4 Drawing Sheets

U.S. PATENT DOCUMENTS

| | | |
|---|---|---|
| 4,207,898 A | 6/1980 | Becht |
| 4,250,873 A | 2/1981 | Bonnet |
| 4,273,109 A | 6/1981 | Enderby |
| 4,273,111 A | 6/1981 | Tsukaya |
| 4,289,131 A | 9/1981 | Mueller |
| 4,289,133 A | 9/1981 | Rothfuss |
| 4,304,236 A | 12/1981 | Conta et al. |
| 4,310,115 A | 1/1982 | Inoue |
| 4,319,576 A | 3/1982 | Rothfuss |
| 4,319,576 A | 3/1982 | Rothfuss |
| 4,351,466 A | 9/1982 | Noiles |
| 4,367,729 A | 1/1983 | Ogiu |
| 4,379,457 A | 4/1983 | Gravener et al. |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,559,928 A | 12/1985 | Takayama |
| 4,566,456 A | 1/1986 | Koning et al. |
| 4,573,468 A | 3/1986 | Conta et al. |
| 4,574,806 A | 3/1986 | McCarthy |
| 4,576,167 A | 3/1986 | Noiles |
| 4,585,000 A | 4/1986 | Hershenson |
| 4,589,412 A | 5/1986 | Kensey |
| 4,589,582 A | 5/1986 | Bilotti |
| 4,592,354 A | 6/1986 | Rothfuss |
| 4,593,679 A | 6/1986 | Collins |
| 4,603,693 A | 8/1986 | Conta et al. |
| 4,606,343 A | 8/1986 | Conta et al. |
| 4,610,383 A | 9/1986 | Rothfuss et al. |
| 4,631,052 A | 12/1986 | Kensey |
| 4,644,952 A | 2/1987 | Patipa et al. |
| 4,646,745 A | 3/1987 | Noiles |
| 4,667,673 A | 5/1987 | Li |
| 4,671,445 A | 6/1987 | Barker et al. |
| 4,672,961 A | 6/1987 | Davies |
| 4,674,515 A | 6/1987 | Andou et al. |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,732,156 A | 3/1988 | Nakamura |
| 4,733,118 A | 3/1988 | Mihalko |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,817,847 A | 4/1989 | Redtenbacher et al. |
| 4,819,632 A | 4/1989 | Davies |
| 4,867,158 A | 9/1989 | Sugg |
| 4,873,977 A | 10/1989 | Avant et al. |
| 4,887,599 A | 12/1989 | Muller |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,955,882 A | 9/1990 | Hakky |
| 4,957,499 A | 9/1990 | Lipatov et al. |
| 4,962,877 A | 10/1990 | Hervas |
| 4,976,710 A | 12/1990 | Mackin |
| 4,994,060 A | 2/1991 | Rink et al. |
| 4,995,877 A | 2/1991 | Ams et al. |
| 5,005,749 A | 4/1991 | Aranyi |
| 5,059,203 A | 10/1991 | Husted |
| 5,071,430 A | 12/1991 | de Salis et al. |
| 5,077,506 A | 12/1991 | Krause |
| 5,104,025 A | 4/1992 | Main et al. |
| 5,133,359 A | 7/1992 | Kedem |
| 5,133,713 A | 7/1992 | Huang et al. |
| 5,133,729 A | 7/1992 | Sjostrom |
| 5,171,247 A | 12/1992 | Hughett et al. |
| 5,171,251 A | 12/1992 | Bregen et al. |
| 5,192,292 A | 3/1993 | Cezana et al. |
| 5,201,325 A | 4/1993 | McEwen et al. |
| 5,201,750 A | 4/1993 | Höcherl et al. |
| 5,205,459 A | 4/1993 | Brinkerhoff et al. |
| 5,207,691 A | 5/1993 | Nardella |
| 5,207,697 A | 5/1993 | Carusillo et al. |
| 5,237,884 A | 8/1993 | Seto |
| 5,249,583 A | 10/1993 | Mallaby |
| 5,258,007 A | 11/1993 | Spetzler et al. |
| 5,261,877 A | 11/1993 | Fine et al. |
| 5,267,997 A | 12/1993 | Farin et al. |
| 5,268,622 A | 12/1993 | Philipp |
| 5,271,544 A | 12/1993 | Fox et al. |
| 5,275,322 A | 1/1994 | Brinkerhoff et al. |
| 5,279,565 A | 1/1994 | Klein et al. |
| 5,285,945 A | 2/1994 | Brinkerhoff et al. |
| 5,290,299 A | 3/1994 | Fain et al. |
| 5,292,053 A | 3/1994 | Bilotti et al. |
| 5,333,773 A | 8/1994 | Main et al. |
| 5,350,104 A | 9/1994 | Main et al. |
| 5,358,506 A | 10/1994 | Green et al. |
| 5,383,880 A | 1/1995 | Hooven |
| 5,395,033 A | 3/1995 | Byrne et al. |
| 5,403,327 A | 4/1995 | Thornton et al. |
| 5,411,508 A | 5/1995 | Bessler et al. |
| 5,433,721 A | 7/1995 | Hooven et al. |
| 5,467,911 A | 11/1995 | Tsuruta et al. |
| 5,518,163 A | 5/1996 | Hooven |
| 5,518,164 A | 5/1996 | Hooven |
| 5,533,661 A | 7/1996 | Main et al. |
| 5,562,702 A | 10/1996 | Huitema et al. |
| 5,591,196 A | 1/1997 | Marin et al. |
| 5,653,374 A | 8/1997 | Young et al. |
| 5,667,517 A | 9/1997 | Hooven |
| 5,696,515 A | 12/1997 | Zyren et al. |
| 5,779,130 A | 7/1998 | Alesi et al. |
| 5,782,396 A | 7/1998 | Mastri et al. |
| 5,868,760 A | 2/1999 | McGuckin, Jr. |
| 5,954,259 A | 9/1999 | Viola et al. |
| 6,119,913 A | 9/2000 | Adams et al. |
| 6,126,058 A | 10/2000 | Adams et al. |
| 6,348,061 B1 * | 2/2002 | Whitman ............... 606/198 |

FOREIGN PATENT DOCUMENTS

| | | |
|---|---|---|
| EP | 0 552 050 | 7/1993 |
| EP | 0 598 579 | 5/1994 |
| EP | 0 705 571 | 4/1996 |
| GB | 2180455 | 4/1987 |
| NL | 77 11 347 | 4/1979 |
| WO | WO 90/05491 | 5/1990 |

* cited by examiner

VESSEL AND LUMEN EXPANDER ATTACHMENT FOR USE WITH AN ELECTROMECHANICAL DRIVER DEVICE

CROSS-REFERENCE TO RELATED APPLICATIONS

This application is a continuation of U.S. patent application Ser. No. 09/510,926, filed on Feb. 22, 2000, now U.S. Pat. No. 6,348,061.

BACKGROUND OF THE INVENTION

1. Field of the Invention

The present invention relates generally to an attachment for use with an electromechanical driver device, and more specifically to a vascular expander device which is insertable, expandable, collapsible, and removable within and from a vascular, lumen, or similar vessel by means of a remote electromechanical driver device.

2. Description of the Prior Art

Upon identification of a stricture and/or stenosis in an artery, gastrointestinal tract, bowel, or other vessel of the body (for another important example, the bile duct) several treatment actions may be selected. Surgical intervention may include fully invasive procedures such as bypasses in which supplemental vessels are transplanted from other regions of the body, or in less frequent circumstances, artificial supplemental structures are implanted. This fully invasive procedure often requires significant hospitalization and tremendous rehabilitation. For these reasons, it has been a goal of the industry to minimize the number of instances in which these procedures are performed to the barest minimum. The less invasive surgical intervention, which has become more desirable, is one in which a device is inserted into the segment of the vessel which has narrowed, and to inflate the device within the segment until the passage through the vessel has been expanded to a more acceptable diameter. This procedure has been widely accepted and is only untenable in situations where the stenosis has occurred to such a great extent that the device cannot be inserted. Target tissues for such procedures, as mentioned above, include cardiovascular arteries which have sclerosed, peripheral vascular arteries which have sclerosed, bowel tissue which has narrowed due to scarring or other narrowing event, to an extent that such sclerosing or narrowing inhibits the proper flow of digestion, and normal use of any other soft tissue vessel which has sufficient elasticity to expand.

While the methodological innovation of expanding a structure within a stenosed vessel to increase flow therethrough to a more desirable level is one of the great advances in medicine of the last few decades, the instruments utilized in the execution of these procedures have lagged substantially behind the development curve. The traditional instrument for such a procedure, for example, a dilation balloon catheter for an angioplasty, is a long flexible tube having a selectively expandable volume disposed in the tip of the device. This tube having the expandable volume in its tip is directed through the femoral artery, the aorta, and into the heart itself. From the heart, it is directed into the partially blocked vessel. Once the tip of the device is disposed in the narrowed channel, a fluid (usually saline) is advanced into the flexible expanding volume to cause it to inflate. The inflating balloon presses against the walls of the vessel, causing them to expand outwardly. This process is continued until the vessel is enlarged to the point that the physician feels that the flow through it will be sufficient to alleviate the symptoms and potential for damage.

One of the most important drawbacks of the balloon catheter design is that the means for inflating the volume, and the manner in which the volume is inflated, completely blocks the flow of fluids through the vessel during the procedure. This failure is inherent in the design by virtue of the fact that the balloon must occlude the vessel in order to apply the pressure to the walls. A few alternative designs have been proposed in the art which provide a minimal solution to the problem by offering a number of cannulae, or narrow and rigid pass through holes, formed in the balloon itself, for permitting a small amount of fluid to flow when the balloon is fully inflated.

This attempted solution further highlights (and exacerbates) the other important failure of balloon type devices. This failure relates to the gathering of information about the expansion of the vessel walls. More particularly, one of the important measurements involved with any vessel expansion is the change in diameter, which is attained at a given internal pressure of the balloon. The relationship of pressure and diameter is inherently imprecise as vessel tissue varies in elasticity across the spectrum of potential patients as well as the degree of expansion or vessel narrowing which has already taken place (for example, a second or third angioplasty might proceed with a completely different pressure to diameter profile from that of a first time procedure). The inclusion of narrow passages through the expanding volume, especially in the case of a balloon having a cannulated structure, results in a very unreliable interior pressure to diameter relationship.

Unfortunately, it is also not always the case that the one time expansion of the vessel (during the surgical intervention) continues to remain effective over a long period. The stenosis of the vessel often continues, and the flow through the treated area may drop again to a level requiring additional intervention. As repeated expansion of the vessel stresses the tissue, and has been linked to the formation of aneurysms, it has been found necessary to install a permanent structural element into the vessel. These structural elements, which are generally referred to as stents, are generally tubular in shape, but are formed in a variety of different manners, including solid cylinders, meshes, fabrics, etc. The introduction of a stent into a patient usually follows a traditional angioplasty procedure, during which the vessel is expanded to the necessary diameter for the stent to be inserted. The remote installation of a stent is difficult, but several designs have been offered in which the stent is delivered in a collapsed form, and is then irreversibly expanded into position by means incorporated into the insertion tube. The diameter of a specific stent is, therefore, predetermined, and the diameter of the stent selected must be picked correctly.

It has been found, however, that over time, the stent is incorporated by the body, into the tissue wall of the vessel. Continued stenosis of the vessel around, and/or through the stent, presents an immediately understandable problem for continued treatment, i.e., the stent is a rigid metal structure which will prevent an angioplasty procedure from being able to expand the vessel (the balloon will expand against the stent, and the stent will remain undeflected).

Removal of a stent which has already been incorporated by the body is a considerable problem. Techniques of sheering off the tissue which has built up on and around the inside of the stent have been provided in the art, however, these generally include a rotating blade within the vessel. The risks of particulate matter becoming dislodged within the vessel, and causing considerable damage as a result, as well as the potential for weakening the structural integrity of the vessel walls to the point of rupture has limited the applicability of this technique. In the final analysis, stents have a tainted usefulness insofar as they may alleviate the stenosed condition for a short period, but may preordain and require a full bypass procedure if the vessel begins to re-stenose (which occurs in a vast number of such cases).

It is also a failure of the present instrumentation that as with many such devices of the prior art, all of these devices are considered fully disposable, and are, in fact, thrown away after a single use. They are complicated devices, having multiple moving parts, requiring substantial structural integrity and, therefore, expense in manufacturing. The fact that they are used only once, and no part can be used again render the use of such devices expensive and wasteful of resources.

In addition to this failure, as can be readily observed from the preceding descriptions, the prior art devices suffer from numerous other limitations, which would be desirable to overcome. These includes the requirement that the surgeon manually actuate all of the features and functions of the balloon catheter and the fact that the angioplasty balloon inflates to a discrete size, necessitating the replacement of an undersized balloon with the next size balloon. This process may be repeated numerous times until the appropriate diameter is achieved. Any and all undersized balloons are wasted during this procedure.

It is, therefore, a principal object of the present invention to provide a device which may be remotely actuated to expand and apply a radially outward pressure against the walls of a narrowed vessel or lumen in conjunction with and in accordance with a surgical procedure.

It is further an object of the present invention to provide an instrument for expanding tissue during gastrointestinal surgery, cardiovascular angioplasty, peripheral vascular angioplasty, and other procedures, which will reduce the waste of resources and facilitate a range of expansion (for example, eliminating the need for sizing the vessels as described above) by permitting use as an attachment to an electromechanical driver device.

It is further an object of the present invention to provide a device which reduces the requirements for the surgeon, gastroenterologist, or cardiologist to manually actuate different components and mechanisms.

It is further an object of the present invention to provide a device which does not occlude the vessel in which it is expanding, thereby permitting a significant flow of fluid to continue as it expands against the vessel or lumen walls.

It is further an object of the present invention that at least a portion of the expanding section of the device be selectively disengageable and implantable within the vessel or lumen if it is determined that the vessel or lumen requires a permanent structural support.

It is further an object of the present invention that the device, and in particular the portion which may be selectively permanently implanted in the vessel or lumen, be expandable through and permanently (and rigidly) expanded to a diameter within a range of different diameters.

Other objects of the present invention shall be recognized in accordance with the description thereof provided hereinbelow in the Summary of the Invention, and in the Detailed Description of Preferred Embodiments in conjunction with the Figures.

SUMMARY OF THE INVENTION

The preceding objects of the invention are provided by an attachment of the present invention which is coupled with, and actuated by, an electromechanical driver device set forth in more complete detail in U.S. Ser. No. 09/324,452, entitled "An Electromechanical Driver Device for use with Anastomosing, Stapling, and Resecting Instruments", assigned to the same assignee of the present invention. More particularly, the attachment may be embodied in a variety of different structures, a preferred one being set forth in more detail hereinbelow. Each embodiment of the attachment, however, is coupleable to the distal end of the flexible shaft of the electromechanical driver device which causes the attachment, among other additional functions, to expand and contract upon proper remote actuation of the electromechanical driver device and in accordance therewith.

More specifically, the electromechanical driver device comprises a handle and a flexible drive shaft. The handle has a pistol grip-styled design, having a finger trigger which is independently coupled to a motor which turns a flexible drive shaft (described more fully hereinbelow). The motor is a dual direction motor, and is coupled to a manual drive switch mounted to the top of the handle, by which the surgeon user can selectively alter the turning direction of the motor. This dual direction capacity may be most simply achieved by selecting a motor which turns in a direction corresponding to the direction of current, and actuation of the manual drive switch alters the direction of the current accordingly. In this example, the power source supplying the motor must be a direct current source, such as a battery pack (and most desirably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current.

In addition to the motor components, the handle may further include several other features, including: (1) a remote status indicator; (2) a shaft steering means; and (3) at least one additional electrical supply. First, the remote status indicator may comprise an LCD (or similar read out device) by which the user may gain knowledge of the position of components (for example whether the spokes are at the closed position or at a definite expanded diameter). Second, the handle also includes a manually actuateable steering means, for example, a joystick or track ball, for directing the movement of the flexible shaft (by means of steering wires implanted in the flexible shaft described more fully hereinbelow). Finally, the handle may include an additional electrical power supply and an on/off switch for selectively supplying electrical power to the attachments.

More particularly, with respect to the flexible shaft, the shaft comprises a tubular sheath, preferably formed of a simple elastomeric material which is tissue-compatible and which is sterilizable (i.e., is sufficiently rugged to withstand an autoclave). Various lengths of this flexible shaft may be provided in conjunction with the present invention. In this case, the flexible shaft and the handle should be separable. If separable, the interface between the proximal end of the flexible shaft and the distal end of the handle should include a coupling means for the drive components.

Specifically regarding the drive components of the flexible shaft, within the elastomeric tubular sheath is a smaller fixed tube which contains a flexible drive shaft which is capable of rotating within the fixed tube. The flexible drive shaft, itself, simply must be capable of translating a torque from the motor in the handle to the distal end of the flexible drive shaft, while still being flexible enough to be bent, angled, curved, etc. as the surgeon deems necessary to "snake" through the vessel of the patient up to the occluded section. For example, the flexible drive shaft may comprise a woven steel fiber cable. It shall be recognized that other flexible drive shafts may be suitable for this purpose.

In order to securely engage an attachment, such as the vessel and lumen expander attachment which is the subject of the present invention (as described more fully hereinbelow), it is preferred that the distal end of the flexible shaft include a stability gripping feature, which preferably is simply a set of prongs which engage a pair of recesses in the coupling end of the attachment (as described more fully hereinbelow). Further, the distal end of the flexible drive shaft must have a conformation which permits the continued translation of torque. For example, the distal end of the flexible drive shaft may be hexagonal, thereby fitting into a hexagonal recess in the coupling interface of the attachment. The distal end of the flexible drive shaft may further include additional topological features which enhance the engagement of the flexible drive shaft to a potential attachment, but which are stationary and thereby provide a stable reference position for applying the rotation to only a portion of the attachment (so that the entire attachment does not rotate when the torque is applied to one portion of the attachment).

As suggested above, in conjunction with the manually actuateable steering means mounted to the handle, the flexible shaft further includes at least two steering wires which are flexible, but which are coupled to the inner surface of the flexible shaft near the distal end thereof. The steering wires may be axially translated relative to one another by actuation of the manually actuateable steering means, which action causes the flexible shaft to bend and curve accordingly.

Also as suggested above, in conjunction with the remote status indicator of the handle, the flexible shaft further contains an electrical lead for coupling to the attachments. This electrical lead channels a signal from the attachment to the handle for indicating the status of the attachment (for example, the diametric extent to which the attachment device has expanded to open the vessel or lumen).

More particularly, with respect to the vessel and lumen expander attachment of the present invention, the attachment has several different potential embodiments, and preferred ones are disclosed herein as examples. The attachment is fitted with at least one linear drive extension, which is most simply described as a turning rod. In both embodiments, this turning rod comprises an elongate cylindrical rod having first and second elongate ends. A discontinuous threading is provided on the outer surface of the rod, and extends from a position which is a short distance from the first end to a position which is a short distance from the second end. The threading is discontinuous insofar as the threading on the upper half of the rod is directed in one direction, and the threading on the lower half is oriented in the opposing direction. A pair of nuts are mounted on the rod, a first nut being mounted on the threading of the upper half, and a second nut being mounted on the threading of the lower half. Rotation of the rod about its elongate axis, therefore, while preventing the nuts from rotating therewith, causes the nuts to either travel towards one another or apart from one another, in accordance with the direction of relative rotation and threading.

At each of the unthreaded elongate ends of the rod is also provided a circumferential recess, in which a washer is mounted. The washers are coupled to one another by elongate pins which extend in parallel with the rod. The washers are mounted to the rod such that the rod may rotate while the washers remain relatively motionless. In fact, the lower washer includes a topological feature which couples to the corresponding stability gripping feature of the flexible shaft of the electromechanical driver device such that the washers do not move relative to the driver mechanism, but such that free rotation of the rod 200 relative to them is not inhibited.

The nuts which are mounted to the rod include at least one tracking hole which mates with the pins which couple the washers together, such that they may travel linearly along the extent of the rod, but are constrained against rotation with the rod.

At the first end of the rod, the radial face of the cylinder includes a joining means (for example, a hexagonal coupling recess) for coupling to the flexible drive shaft of the electromechanical driver device. That is, when the attachment is mated to the electromechanical driver device, the rod is in mechanical communication with the flexible drive shaft such that the activation of the motor of the electromechanical driver device activates the rod, causing the nuts to travel along the rod, either toward one another, or away from one another in accordance with the specific orientations of the threading.

In a preferred embodiment, each of the two nuts are coupled to one another at a plurality of circumferential sites by means of a series of flexible joints. More particularly, each of the joints is formed by a pair of spokes, one of which is attached to the first nut at a circumferential site thereon, and the other being similarly mounted on the second nut. Each spoke is fixed at one end to its respective nut by a joint which permits the spoke to rotate radially outwardly. At the other end of each spoke, each is coupled by a similar joint to the distal end of a corresponding opposing spoke, such that the connected spokes may expand radially outwardly in an umbrella-like fashion, when the nuts are brought together, and swing radially inwardly when the nuts travel apart. It shall be understood that the spokes need not be directly coupled with one another, but instead may be coupled together by a third pin which is jointed with the distal ends of the spokes, and moves radially with respect to the rod in accordance with the motion of the nuts, but which remains parallel to the rod.

The distal ends of the spokes are also coupled with a flexible tubular material which forms a continuous expanding surface as the nuts are brought together. More particularly, the flexible tube, or shroud, includes sufficient axial rigidity (for example, by means of axial ribs), but sufficient radial expandability such that the expanding spokes create a cylindrical structure having a constant diameter and a series of radially spaced apart spokes extending from the inner surface of the flexible shroud to the central axis of the rod. In the version of this embodiment in which the spokes are separately jointed with the interior surface of the cylindrical structure, there are at least two axially separate groups of radially spaced apart spokes extending from the inner surface of the flexible shroud to the central axis of the rod. Inasmuch as the flexible shroud does not include a radially facing surface at either axial end thereof, only the rod and the spokes inhibit the free passage of fluid through the vessel as the expansion is being provided.

It shall be further understood that the invention may be constructed and coupled to the flexible drive shaft in such a way that once the attachment has been expanded to the proper amount (in an analog manner), it may be decoupled and remain as a permanent stent in the vessel or lumen.

Future collapse and removal of the stent may be possible, or at least affected in a less destructive manner than other stents of the prior art, especially stents which are not collapsible.

In practice, this attachment may be utilized in the following manner. The surgeon user begins by coupling the attachment to the distal end of the flexible shaft of the electromechanical driver and making certain that the nuts have been extended to their farthest possible separation such that the flexible shroud is in its most radially compact form. The flexible shaft and attachment are then introduced into the vessel or lumen at the desired point of entry, for example into the femoral artery in the case of a blockage of a cardiovascular vessel in the vicinity of the heart. The flexible shaft and attachment are then advanced up to and through the partially occluded section of the vessel or lumen. The guidance of the flexible shaft up through the vessel or lumen is provided by remote steering wire actuation in the handle of the electromechanical driver device (as described more fully hereinabove, and in U.S. patent application Ser. No. 09/324,452, identified above). As mentioned above, this attachment, and in fact, this entire procedure is best applicable in circumstances in which the patient does not have complete blockage of the vessel, inasmuch as it is necessary to advance the attachment into the occluded section.

Once the attachment is properly positioned, the surgeon begins by actuating the finger trigger in the handle of the electromechanical driver device, causing the flexible drive shaft within the flexible shaft to rotate. The coupling of the attachment with the distal end of the flexible drive shaft causes the discontinuously threaded elongate rod to rotate (and only the discontinuously threaded elongate rod). The nuts then advance towards one another, causing the spokes to rotate outward and to radially open the flexible tube thereby pressing against the occluded vessel walls and radially opening the vessel to permit greater fluid flow. In conjunction with the versions of this embodiment in which the attachment may be remotely decoupled from the distal end of the flexible shaft of the electromechanical driver device, it may be found appropriate by the surgeon to leave the expanded stentlike structure in place to at least slow the potential re-stenosis of the vessel.

A DETAILED DESCRIPTION OF THE PREFERRED EMBODIMENTS

While the present invention will be described more fully hereinafter with reference to the accompanying drawings, in which particular embodiments are shown, and with respect to methods of use, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

More particularly, the present invention comprises a vessel and lumen expander attachment for use with an electromechanical driver device. In order to fully understand the use and function of the attachment it is useful to discuss the electromechanical driver device. Therefore, referring now to FIG. 1, the electromechanical driver device is described hereinbelow. The electromechanical driver device has a handle portion 102 and a flexible drive shaft portion 104. The handle 102 includes a portion which is shaped in a manner which is easily gripped by the surgeon operator. For example, in the embodiment provided herein, the handle 102 comprises a pistol grip-styled portion 106. The grip portion 106 includes at least one, and in the present embodiment exactly one, finger actuateable trigger 108. The finger trigger 108 is coupled to a motor 110 housed within the interior volume of the handle 102, which turns a flexible drive shaft (described more fully, hereinbelow).

Figure 1:
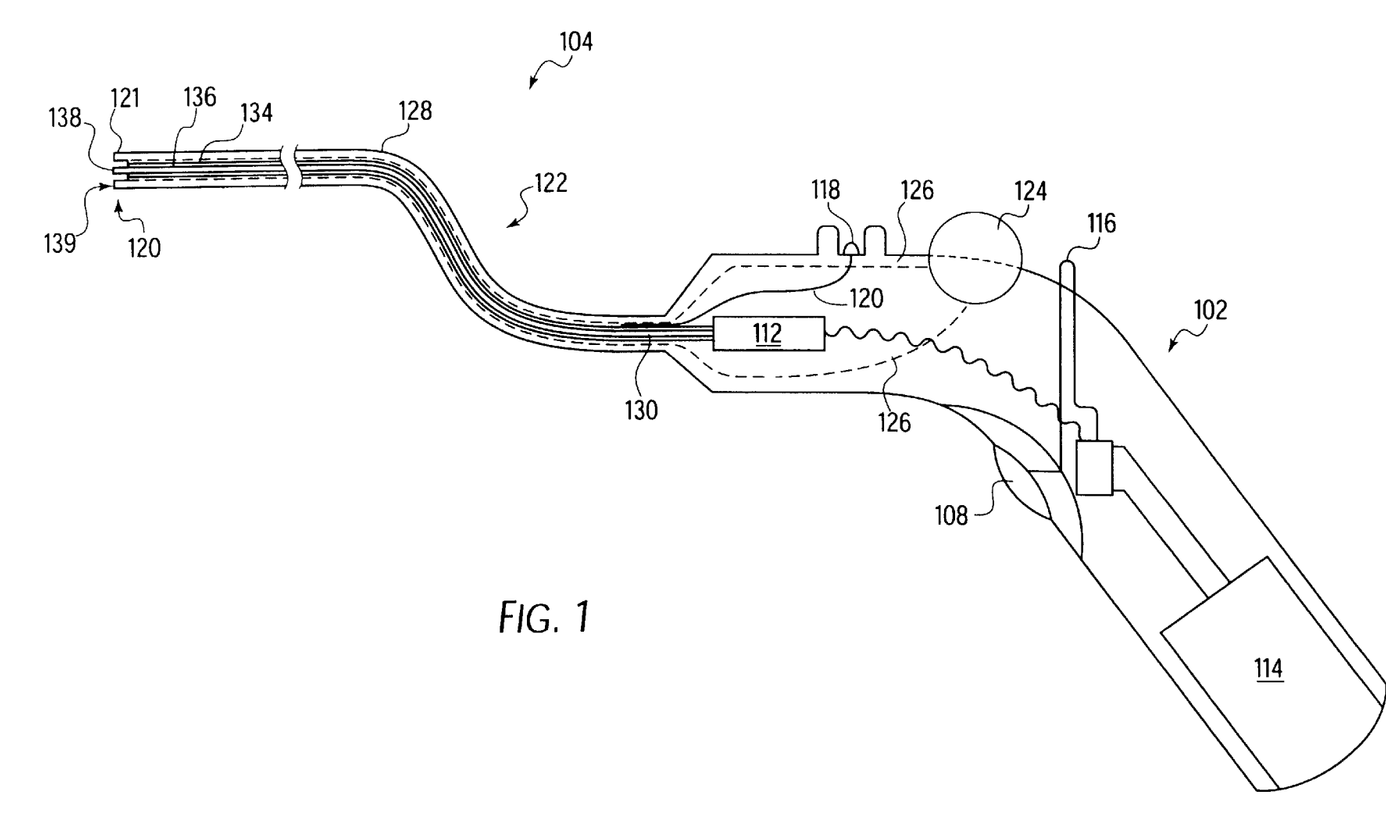
FIG. 1 is a side view of a handle and flexible shaft of the present invention, wherein internal features of the elements are provided in phantom.

More particularly, with respect to the motor 112, it is a dual direction motor coupled to a manual drive switch 116 and powered by a power source 114. The manual drive switch 116 is provided on the top of the handle 100, such that the surgeon user can selectively alter the turning direction of the motor 112, and thereby, the flexible shaft 122. It shall be understood that alternative power sources, including dual direct current sources or single remote alternating current sources (such as the alternating current provided from standard United States 120 Volt, 60 Hertz wall outlets) may be used in conjunction with alternative embodiments. In the event that the electromechanical driver device should be useable with an alternating current, either a transformer can be included between the motor 112 and the power source 114, or a more sophisticated intermediate gearing assembly may be provided between the motor 112 and the flexible drive shaft 136.

In addition to the motor 110 and related power and drive switch elements, the handle 100 further include a remote status indicator 118 which may comprise an LCD (or similar read out device) by which the user may gain knowledge of the position of components (for example whether the spokes are at the closed position or at a definite expanded diameter). The handle 100 further includes a manually actuateable steering means 124 for causing the remote movement of the distal end 121 of the flexible shaft 122, which in the present embodiment comprises a trackball 124, coupled to a plurality of steering wires 126. The steering wires 126 extend along the flexible shaft 122 (described more fully hereinbelow) and are coupled to the distal end 121 of the flexible shaft 122. When the trackball 124 is rotated, the steering wires 126 are pulled, and the distal end 121 of the flexible shaft 122 turns correspondingly.

More particularly, with respect to the flexible shaft 122, the shaft comprises a tubular sheath 128 which is formed of a tissue-compatible, elastomeric material. As this device is to be reused, it is important that the material be sterilizable (i.e., is sufficiently rugged to withstand an autoclave). While the embodiment illustrated comprises a contiguous handle 102 and flexible shaft 122, it shall be understood that one having ordinary skill in the art may provide an alternative embodiment having a separable handle 102 and flexible shaft 122, thus permitting alternative shaft lengths for alternative purposes. In such cases, the flexible shaft 122 and the handle 100 should include an interface between the proximal end of the flexible shaft 122 and the distal end of the handle 100 which should include a coupling means for the drive components.

Specifically regarding the drive components 130 of the flexible shaft 122, within the elastomeric tubular sheath 128 is a smaller fixed tube 134 which contains a flexible drive shaft 136 which is capable of rotating within the fixed tube 134. The flexible drive shaft 136, itself, simply must be capable of translating a torque from the motor 112 in the handle 102 to the distal end 138 of the flexible drive shaft 136, while still being flexible enough to be bent, angled, curved, etc. as the surgeon deems necessary to "snake" the attachment through the vessel of the patient. For example, the flexible drive shaft 136 may comprise a woven steel fiber cable, a high tensile strength polymeric material, or a sufficiently flexible unitary metal shaft.

Figure 2:
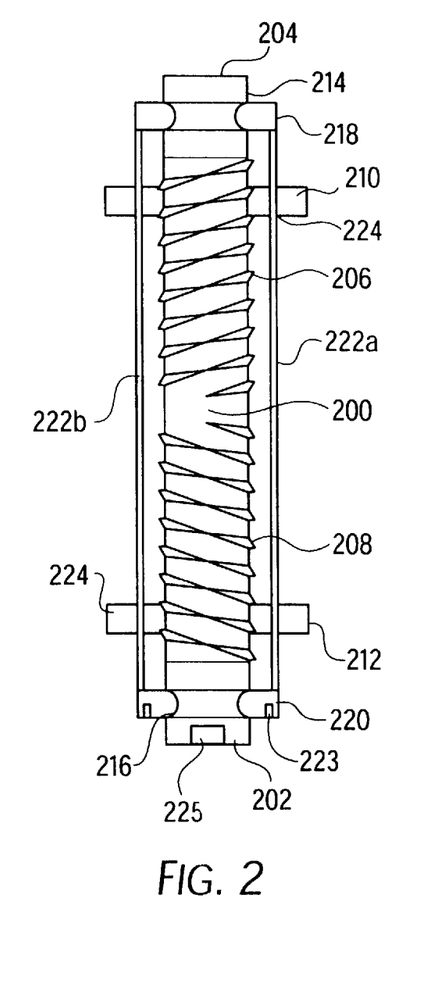
FIG. 2 is a side view of the discontinuously threaded elongate rod, nuts and washer subassembly, which is an aspect of the present invention.
Figure 3A:
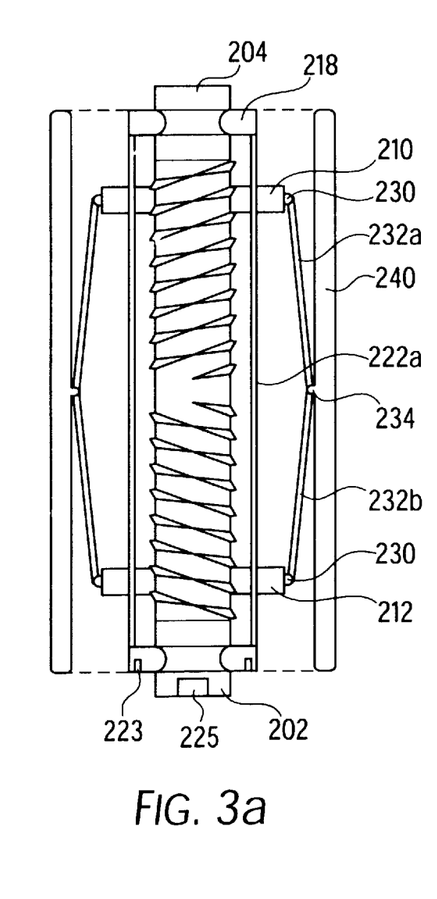
FIGS. 3a and 3b are side cross-section views of one version of present invention in which the complete attachment assembly is in closed and expanded dispositions, respectively.
Figure 3B:
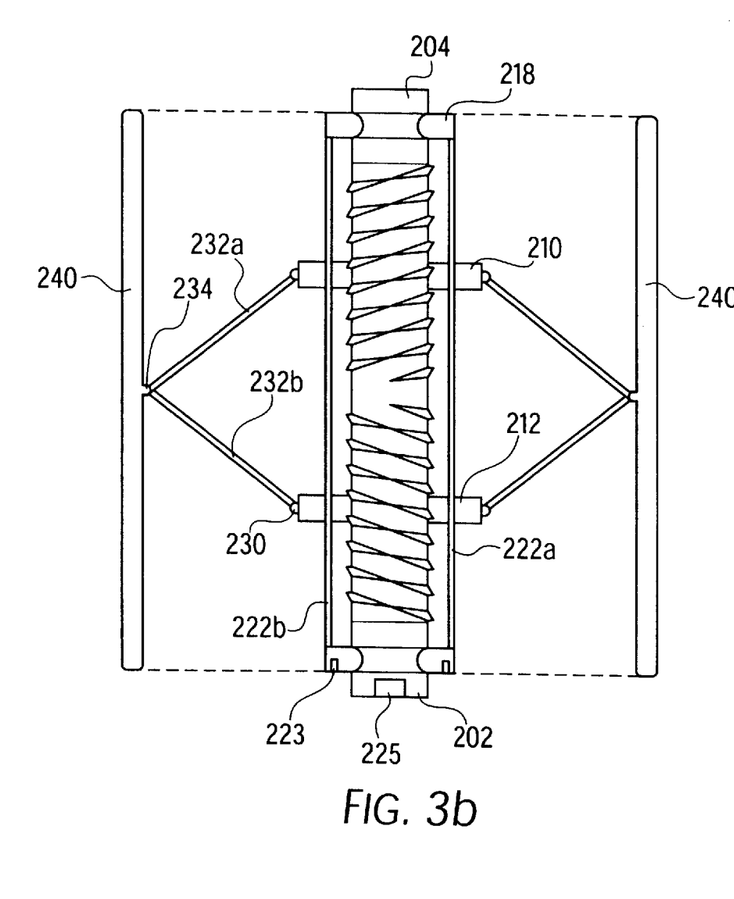
Figure 4A:
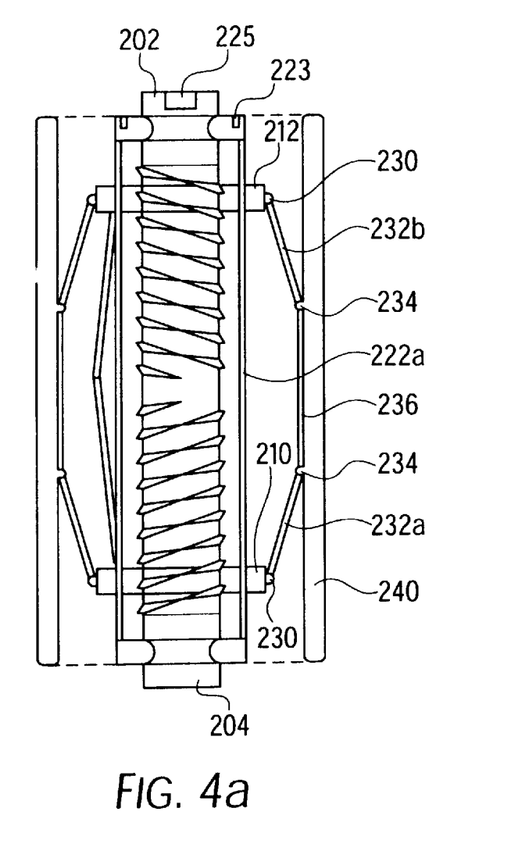
FIGS. 4a and 4b are side cross-section views of another version of the present invention in which the attachment assembly is in semi-expanded and fully expanded dispositions.
Figure 4B:
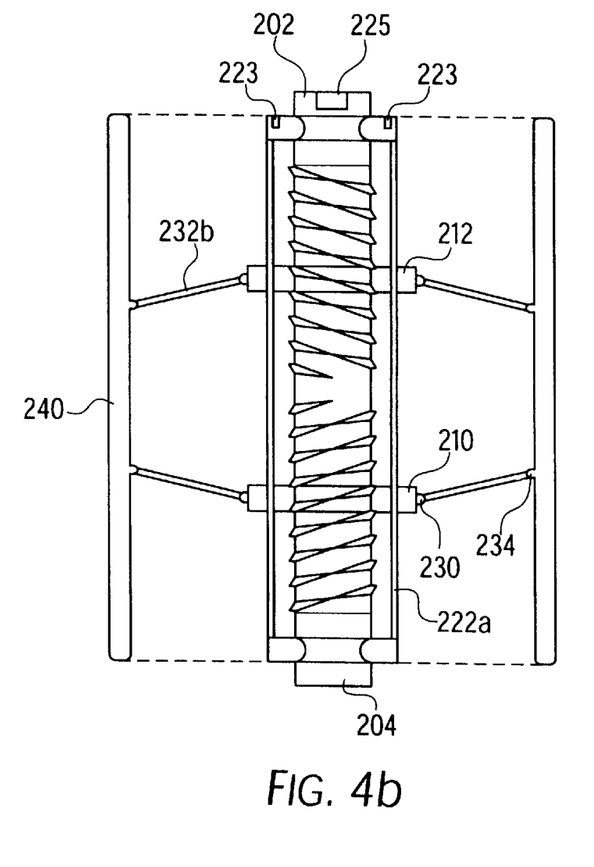

In order to securely engage the attachment to be used with this electromechanical driver device, it is preferred that the distal end 121 of the flexible shaft 122 include a stability gripping feature 139, which preferably is simply a set of prongs which engage a pair of recesses in the coupling end of the attachment (see FIGS. 2–4).

In order for the distal end 138 of the flexible drive shaft 136 to couple with the attachment, the distal end 138 of the flexible drive shaft 136 must have a conformation which permits the continued translation of torque. In the present embodiment, this coupling is achieved by a geometric fitting, and more precisely, the distal end 138 of the flexible drive shaft 136 is hexagonal, and thereby fits into a hexagonal recess in the coupling interface of the attachment (see FIG. 2). The remainder of the distal end 138 which is not the flexible drive shaft 136, and which does not move, includes a stable junction feature 139 which may also couple with the selected attachment in such a manner as to prevent portions of the attachment which are not to turn in accordance with the rotation of the flexible drive shaft 136 from turning.

In conjunction with the manually actuateable steering means 124 mounted to the handle 102, the flexible shaft 122 further includes at least two steering wires 126 which are flexible, but which are coupled to the inner surface of the flexible shaft 122 near the distal end thereof. The steering wires 126 may be axially translated relative to one another by actuation of the manually actuateable steering means 124, which action causes the flexible shaft 122 to bend and curve accordingly.

In conjunction with the remote status indicator 118 of the handle 102, the flexible shaft 122 further contains an electrical lead 120 for coupling to the attachments. This electrical lead 120 channels a signal from the attachment to the handle 102 for indicating the status of the attachment (for example, the diametric extent to which the attachment has expanded to open the vessel or lumen).

Referring now to FIG. 2, the vessel and lumen expander attachment is fitted with a linear drive extension, or turning rod 200. In both embodiments to be described herein, this turning rod 200 comprises an elongate cylindrical rod 200 having first and second elongate ends 202, 204, respectively. A discontinuous threading 206, 208 is provided on the outer surface of the rod 200, and extends from a position which is a short distance from the first elongate end 202 to a position which is a short distance from the second elongate end 204. The threading is discontinuous insofar as the threading 206 on the upper half of the rod is directed in one direction, and the threading 208 on the lower half is oriented in the opposite direction. A pair of nuts 210, 212 are mounted on the rod 200, the first nut 210 being mounted on the threading 206 of the upper half, and a second nut 212 being mounted on the threading 208 of the lower half. Rotation of the rod 200 about its elongate axis, therefore, while preventing the nuts 210, 212 from rotating therewith, causes the nuts 210, 212 to either travel towards one another or apart from one another, in accordance with the direction of relative rotation and threading.

At each of the unthreaded elongate ends 202, 204 of the rod 200 is also provided a circumferential recess 214, 216, respectively, in which a washer 218, 220 is mounted. The washers 218, 220 are coupled to one another by elongate pins 222a, 222b which extend in parallel with the elongate cylindrical rod 200. The washers 218, 220 are mounted to the rod 200 such that the rod 200 may rotate while the washers 218, 200 remain relatively motionless. In fact, the lower washer 220 includes a pair of recesses 223 which couple to the corresponding stability gripping feature (best shown as item 139 on FIG. 1) of the flexible shaft of the electromechanical driver device such that the washers 218, 220 do not move relative to the driver mechanism, but such that free rotation of the rod 200 relative to them is not inhibited.

The nuts 210, 212 which are mounted to the rod 200 include a pair of tracking holes 224 through which the elongate pins 222a, 222b couple the washers 218, 200 together, such that the nuts 210, 212 may travel linearly along the extent of the rod 200, but are constrained against rotation with the rod 200.

At the first end 202 of the rod 200, the radial face of the cylinder includes a coupling recess 225 (for example, a hexagonal socket) for coupling to the flexible drive shaft of the electromechanical driver device. That is, when the attachment is mated to the electromechanical driver device, the rod 200 is in mechanical communication with at least one flexible drive shaft such that the activation of the motors of the electromechanical driver device activates the rod, causing the nuts 210, 212 to travel along the rod 200, either toward one another, or away from one another in accordance with the specific orientations of the threading.

Referring now to FIGS. 3a and 3b, a first embodiment of the present invention is provided in a pair of cross-sectional views; the first illustrating the attachment in a semi-expanded position, and the second illustrating the attachment in a fully extended position. In this embodiment, each of the nuts 210, 212 are coupled to one another at a plurality of circumferential sites by means of a series of flexible joints, or pivots 230. More particularly, each of the pivots 230 is formed by a pair of spokes 232a, 232b, one 232a of which is attached to the first nut 210 at a circumferential site thereon, and the other 232b being similarly mounted on the second nut 212. Each spoke 232a, 232b is fixed at one end to its respective nut 210, 212 by a joint which permits the spoke to rotate radially outwardly. At the other end of each spoke 232a, 232b, each is coupled by a similar joint 234 to the distal end of the corresponding opposing spoke, such that the connected spokes may expand radially outwardly in an umbrella-like fashion, when the nuts 210, 212 are brought together, and swing radially inwardly when the nuts 210, 212 travel apart.

Referring now to FIGS. 4a and 4b, a second embodiment is shown. It shall be understood that the spokes 232a, 232b need not be directly coupled with one another, but instead may be coupled together by a third pin 236 which is jointed with the distal ends of the spokes 232a, 232b, and which moves radially with respect to the rod 200 in accordance with the motion of the nuts 210,212, but which remains parallel to the rod 200.

In both embodiments, the distal ends of the spokes 232a,232b are also coupled with a flexible tubular material 240 which forms a continuous expanding surface as the nuts 210,212 are brought together. More particularly, the flexible tube 240 includes sufficient axial rigidity (for example, by means of axial ribs, not shown), but sufficient radial expandability such that the expanding spokes 232a,232b create a cylindrical structure having a constant diameter and a series of radially spaced apart spokes extending from the inner surface of the flexible tube 240 to the central axis of the rod 200. In the version of this embodiment in which the spokes 232a,232b are separately jointed with the interior surface of the cylindrical structure, there are at least two axially separate groups of radially spaced apart spokes extending from the inner surface of the flexible tube 240 to the central axis of the rod 200. Inasmuch as the flexible tube 240 does not include a radially facing surface (a closed top or bottom of the cylinder) at either axial end thereof, only the central rod 200 and the spokes inhibit the free passage of fluid through the vessel as the expansion is being provided.

It shall be further understood that the invention may be constructed and coupled to the flexible shaft of the electromechanical driver in such a way that once the attachment has been expanded to the proper amount (in an analog manner), it may be decoupled and remain as a permanent stent in the vessel. Future collapse and removal of the stent may be possible, or at least affected in a less destructive manner than other stents of the prior art, especially stents which are not collapsible.

In practice, this attachment may be utilized in the following manner. The surgeon user begins by coupling the attachment to the distal end of the flexible shaft of the electromechanical driver device, making certain that the nuts 210, 212 have been extended to their farthest possible separation such that the flexible tube 240 is in its most radially compact form. The flexible shaft and the attachment are then introduced into the vessel or lumen at the desired point of entry, for example, into the femoral artery in the case of a blockage of a cardiovascular vessel in the vicinity of the heart. The flexible shaft and the attachment are then advanced up to and through the partially occluded section of the vessel. The guidance of the flexible shaft up through the vessel is provided by remote steering wire actuation in the handle of the electromechanical driver device (as described more fully hereinabove, and in U.S. patent application Ser. No. 09/324,452, identified above). As mentioned above, this attachment, and in fact, this entire procedure is best applicable in circumstances in which the patient does not have complete blockage of the vessel, inasmuch as it is necessary to advance the attachment into the occluded section.

Once the attachment is properly positioned, the surgeon begins by actuating the finger trigger in the handle of the electromechanical driver device, causing the flexible drive shaft within the flexible shaft of the electromechanical driver device to rotate. The coupling of the attachment with the distal end of the flexible shaft causes the discontinuously threaded elongate rod 200 (and only the discontinuously threaded elongate rod) to rotate. The nuts 210,212 then advance towards one another, causing the spokes 232a,232b to rotate outward and to radially open the flexible tube 240, thereby pressing against the occluded vessel or lumen walls and radially opening the vessel or lumen to permit greater fluid flow.

In conjunction with the versions of this embodiment in which the attachment may be remotely decoupled from the distal end of the flexible shaft of the electromechanical driver device, it may be found appropriate by the surgeon to leave the expanded stent-like structure in place to at least slow the potential re-stenosis of the vessel or lumen.

While there has been described and illustrated new and novel attachments for use with electromagnetic driver surgical instruments for radially expanding occluded vessels and lumens, it will be apparent to those skilled in the art that variations and modifications are possible without deviating from the broad spirit and principle of the present invention which shall be limited solely by the scope of the claims appended hereto.

What is claimed is:

1. A vessel and lumen expanding attachment for use with an electromechanical driver having a drive shaft including a torque transferring tip, comprising:

a rotatable rod having a first axial portion and a second axial portion, the rod mateable with the torque transferring tip and including a first threading disposed on the first portion and a second threading disposed on the second portion, the first threading oriented in opposition with the second threading;

a first nut and a second nut respectively engaged with the first threading and the second threading;

an arrangement configured to constrain the first nut and the second nut from rotating relative to the rod, rotation of the rod configured to cause the first nut and second nut to travel axially toward each other when the rod is rotated in a first direction and to travel axially away from each other when the rod is rotated in a second direction opposite to the first direction;

a plurality of jointed radially expandable and retractable spokes coupled to the first nut and the second nut, the spokes configured to expand and retract in accordance with the relative axial travel of the first nut and the second nut; and a radially flexible tubular shroud mounted about the rod, the first nut, the second nut and the spokes, the shroud coupled on an interior surface to the spokes and configured to radially expand and contract in accordance with the rotation of the rod.

2. The vessel and lumen expanding attachment according to claim 1, wherein the arrangement includes a pair of washers and at least one pin, the washers mounted at opposing axial ends of the rod and mounted so that rotation of the rod does not cause rotation of the washers, the washers coupled to one another by the pin, the pin extending in parallel with the rod and extending through the first nut and the second nut, the pin configured to form a track along which the first nut and the second nut travel and configured to constrain the first nut and the second nut against rotational.

3. The vessel and lumen expanding attachment according to claim 1, wherein the shroud includes axially rigid ribs configured to support the shroud in an axially constant diameter disposition.

4. The vessel and lumen expanding attachment according to claim 1, wherein each spoke includes:

a pair of elongate members including a distal end and a proximal end, the proximal end pivotably coupled at a position on an outer lateral surface of a respective one of the first nut and the second nut to permit the corresponding elongate member to pivot, the corresponding elongate member swingable through a range of positions including a position parallel to the rod and radially outwardly to a position perpendicular to the rod; and the distal ends of the elongate members coupled to form a pivot joint so that the pair of elongate members are swingable together from a position parallel to the rod and a position perpendicular to the rod as the first nut and the second nut move toward one another in accordance with actuation of the electromechanical driver, the pivot joint configured to move radially outwardly from the rod.

5. The vessel and lumen expanding attachment according to claim 4, wherein a length of the elongate members is selected so that the pivot joint does not move axially relative to the rod.

6. The vessel and lumen expanding attachment according to claim 4, wherein the pivot joint is coupled to the shroud at an inner surface thereof.

7. The vessel and lumen expanding attachment according to claim 1, wherein each spoke includes:
- a first elongate member and a second elongate member, each having a distal end and a proximal end, each proximal end pivotably coupled at a position on an outer lateral surface of a respective one of the first nut and the second nut to permit the corresponding elongate member to pivot, the corresponding elongate member swingable through a range of positions including a position parallel to the rod and radially outwardly to a position perpendicular to the rod;
- a third elongate member oriented in parallel to the rod; and
- a distal end of each of the first elongate member and the second elongate member coupled to opposing ends of the third elongate member to form a pair of pivot joints, each of the first elongate member and the second elongate member swingable from an orientation parallel to the rod and an orientation perpendicular to the rod as the first nut and the second nut move toward each other in accordance with actuation of the electromechanical driver, the pivot joints configured to cause the third elongate member to move radially outwardly from the rod.

8. The vessel and lumen expanding attachment according to claim 7, wherein a length of the first elongate member, a length of the second elongate member and a length of the third elongate member are selected so that the third elongate member does not move axially relative to the rod.

9. The vessel and lumen expanding attachment according to claim 7, wherein the third elongate member is coupled to the shroud at an inner surface thereof.

10. A vessel and lumen expanding attachment configured to couple to an electromechanical driver device, the electromechanical driver device including a rotatable drive shaft, comprising:
- a rotatable rod configured to couple to the rotatable drive shaft and rotate in accordance with a rotation of the rotatable drive shaft, the rod including a first threading and a second threading in opposed orientation;
- a first nut threadingly engaged with the first threading and nonrotatably and axially displaceably engaged with the rod;
- a second nut threadingly engaged with the second threading and nonrotatably and axially displaceably engaged with the rod, rotation of the rod configured to effect axial displacement of the first nut and the second nut toward and away from each other in accordance with a direction of rotation of the rod;
- a plurality of radially expandable and retractable spokes coupled to the first nut and the second nut, the spokes configured to expand and contract in accordance with the axial displacement of the first nut and the second nut; and
- a tubular shroud having an interior surface coupled to the spokes, the shroud configured to radially expand and contract in accordance with the rotation of the rod.

11. The vessel and lumen expanding attachment according to claim 10, further comprising a first washer mounted at a first end of the rod, a second washer mounted at a second end of the rod opposite to the first end and at least one pin coupled to the first washer and the second washer, the pin arranged parallel to the rod and extending through the first nut and the second nut, the pin configured to constrain the first nut and the second nut against rotation.

12. The vessel and lumen expanding attachment according to claim 10, further comprising at least one rib configured to support the shroud.

13. The vessel and lumen expanding attachment according to claim 10, wherein each spoke includes a first member having a distal end and a proximal end and a second member having a distal end and a proximal end, the proximal end of the first member pivotably coupled to the first nut, the proximal and of the second member pivotably coupled to the second nut, the distal end of the first member pivotably coupled to the distal end of the second member.

14. The vessel and lumen expanding attachment according to claim 13, wherein a length of each of the first member and the second member is selected so that a location of the pivotable coupling between the distal ends of the first member and the second member is axially fixed relative to the rod.

15. The vessel and lumen expanding attachment according to claim 13, wherein the distal end of the first member and the distal end of the second member are pivotably coupled to an inner surface of the shroud.

16. The vessel and lumen expanding attachment according to claim 10, wherein each spoke includes a first member having a distal end and a proximal end, a second member having a distal end and a proximal end and a third member arranged parallel to the rod and having a first end and a second end, the proximal end of the first member pivotably coupled to the first nut, the distal end of the first member pivotably coupled to the first end of the third member, the proximal end of the second member pivotably coupled to the second nut, the distal end of the second member pivotably coupled to the second end of the third member; and
- wherein the first member, the second member and the third member are arranged so that rotation of the rod causes the third rod to move radially outwardly from and radially inwardly toward the rod in accordance with the direction of rotation of the rod.

17. The vessel and lumen expanding attachment according to claim 16, wherein the third member is configured to maintain parallel correspondence with the rod during radial movement thereof.

18. The vessel and lumen expanding attachment according to claim 16, wherein a length of each of the first member, the second member and the third member is selected so that the third member does not move axially relative to the rod.

19. The vessel and lumen expanding attachment according to claim 16, wherein the third member is coupled to an inner surface of the shroud.

20. A surgical device, comprising:
- an electromechanical driver;
- a drive shaft coupled to the electromechanical driver;
- a vessel and lumen expanding attachment coupled to the drive shaft, the vessel and lumen expanding attachment including:

a rotatable rod configured to be coupled to the rotatable drive shaft and rotated in accordance with a rotation thereof, the rod including a first threading and a second threading, the first threading and the second threading in opposed orientation;

a first nut configured to threadingly engage the first threading and to nonrotatably and axially displaceably engage the rod;

a second nut configured to threadingly engage the second threading and to nonrotatably and axially displaceably engage the rod, rotation of the rod configured to effect axial displacement of the first nut and the second nut toward and away from each other in accordance with a direction of rotation of the rod;

a plurality of radially expandable and retractable spokes coupled to the first nut and the second nut, the spokes configured to expand and contract in accordance with the axial displacement of the first nut and the second nut; and a tubular shroud having an interior surface coupled to the spokes, the shroud configured to radially expand and contract in accordance with the rotation of the rod.

21. The surgical device according to claim 20, wherein the vessel and lumen expanding attachment further includes a first washer mounted at a first end of the rod, a second washer mounted at a second end of the rod opposite to the first end and at least one pin coupled to the first washer and the second washer, the pin arranged parallel to the rod and extending through the first nut and the second nut, the pin configured to constrain the first nut and the second nut against rotation.

22. The surgical device according to claim 20, wherein the vessel and lumen expanding attachment further includes at least one rib configured to support the shroud.

23. The surgical device according to claim 20, wherein each spoke includes a first member having a distal end and a proximal end and a second member having a distal end and a proximal end, the proximal end of the first member pivotably coupled to the first nut, the proximal and of the second member pivotably coupled to the second nut, the distal end of the first member pivotably coupled to the distal end of the second member.

24. The surgical device according to claim 23, wherein a length of each of the first member and the second member is selected so that a location of the pivotable coupling between the distal ends of the first member and the second member is axially fixed relative to the rod.

25. The surgical device according to claim 23, wherein the distal end of the first member and the distal end of the second member are pivotably coupled to an inner surface of the shroud.

26. The surgical device according to claim 20, wherein each spoke includes a first member having a distal end and a proximal end, a second member having a distal end and a proximal end and a third member arranged parallel to the rod and having a first end and a second end, the proximal end of the first member pivotably coupled to the first nut, the distal end of the first member pivotably coupled to the first end of the third member, the proximal end of the second member pivotably coupled to the second nut, the distal end of the second member pivotably coupled to the second end of the third member; and wherein the first member, the second member and the third member are arranged so that rotation of the rod causes the third rod to move radially outwardly from and radially inwardly toward the rod in accordance with the direction of rotation of the rod.

27. The surgical device according to claim 26, wherein the third member is configured to maintain parallel correspondence with the rod during radial movement thereof.

28. The surgical device according to claim 26, wherein a length of each of the first member, the second member and the third member is selected so that the third member does not move axially relative to the rod.

29. The surgical device according to claim 26, wherein the third member is coupled to an inner surface of the shroud.

* * * * *